(12) United States Patent
Decitre et al.

(10) Patent No.: US 8,866,472 B2
(45) Date of Patent: Oct. 21, 2014

(54) DEVICE FOR DETECTION OF AT LEAST ONE DEFECT IN A CONCAVE OR CONVEX STRUCTURE

(75) Inventors: Jean-Marc Decitre, Marcoussis (FR); Olivier Casula, Longpont sur Orge (FR); Gerard Cattiaux, Chateaufort (FR)

(73) Assignees: Commissariat à l' énergie Atomique et aux énergies Alternatives, Paris (FR); Institut de Radioprotection et de Surete Nucleaire, Fontenay aux roses (FR)

(*) Notice: Subject to any disclaimer, the term of this patent is extended or adjusted under 35 U.S.C. 154(b) by 234 days.

(21) Appl. No.: 13/386,041

(22) PCT Filed: Jul. 28, 2010

(86) PCT No.: PCT/EP2010/060935
§ 371 (c)(1),
(2), (4) Date: Jan. 20, 2012

(87) PCT Pub. No.: WO2011/012639
PCT Pub. Date: Feb. 3, 2011

(65) Prior Publication Data
US 2012/0126801 A1    May 24, 2012

(30) Foreign Application Priority Data
Jul. 30, 2009 (FR) ..................... 09 55341

(51) Int. Cl.
*G01N 27/82* (2006.01)
*G01N 27/90* (2006.01)

(52) U.S. Cl.
CPC ............. *G01N 27/902* (2013.01); *G01N 27/82* (2013.01)
USPC .................................................. 324/238

(58) Field of Classification Search
USPC ............................................. 324/238
See application file for complete search history.

(56) References Cited

U.S. PATENT DOCUMENTS

| 8,159,217 | B2 | 4/2012 | Decitre |
| 2003/0164698 | A1 | 9/2003 | Paulson et al. |
| 2003/0173959 | A1 | 9/2003 | Paulson et al. |
| 2004/0004475 | A1 | 1/2004 | Goldfine et al. |
| 2006/0132123 | A1 | 6/2006 | Wang et al. |

(Continued)

FOREIGN PATENT DOCUMENTS

| EP | 1 674 860 | 6/2006 |
| WO | 2008 156628 | 12/2008 |

OTHER PUBLICATIONS

International Search Report issued on Dec. 3, 2010 in PCT/EP10/060935 filed on Jul. 28, 2010.

*Primary Examiner* — Bot Ledynh
(74) *Attorney, Agent, or Firm* — Oblon, Spivak, McClelland, Maier & Neustadt, L.L.P.

(57) ABSTRACT

A device for detection of at least one defect in a concave or convex structure including an emitting part and a receiving part, in which the emitting part includes at least one current layer that makes it possible to create currents oriented approximately along a same direction as the defects whose influence is to be minimized and the receiving part includes at least one magnetic field receiver, added on or etched on a flexible support.

14 Claims, 13 Drawing Sheets

(56) References Cited

U.S. PATENT DOCUMENTS

| | | |
|---|---|---|
| 2007/0222439 A1 | 9/2007 | Wang et al. |
| 2009/0001974 A1 | 1/2009 | Sheiretov et al. |
| 2010/0109658 A1 | 5/2010 | Decitre |
| 2012/0019239 A1 | 1/2012 | Decitre |
| 2013/0014589 A1* | 1/2013 | Sheiretov et al. ............... 73/765 |

* cited by examiner

DEVICE FOR DETECTION OF AT LEAST ONE DEFECT IN A CONCAVE OR CONVEX STRUCTURE

TECHNICAL FIELD

The invention relates to a device for the detection of at least one defect in a concave or convex structure, for example a cylindrical structure.

STATE OF PRIOR ART

The field of this invention is the detection of defects in concave or convex structures. It is particularly applicable to the detection of defects such as cracks in a tube, for example a steam generator (SG) tube in a nuclear power station. These defects are essentially circumferential or transverse defects that can cause rupture of the tube regardless of the conditions encountered, namely:

- in the presence of a variation in the tube diameter (Expansion Transition Zone (ZTD)); eddy current sensors are efficient provided that there is no variation in the air gap during the inspection,
- and/or in the presence of a longitudinal defect superposed on the circumferential defect being searched.

The field of the invention is for example an expertise inspection of a tube in a steam generator from the internal surface of the tube, more easily accessible on site in the presence of:

- tube deformation zones (expansion transition zone, ovalling),
- complex defects: a "complex defect" is a defect composed of the superposition of at least one longitudinal defect and at least one external transverse defect (typically with a height of 40% of the thickness of the steam generator tube) (in the form of a cross, T or L),
- spacer plates used to hold the tubes in place.

Figures 1, 2:
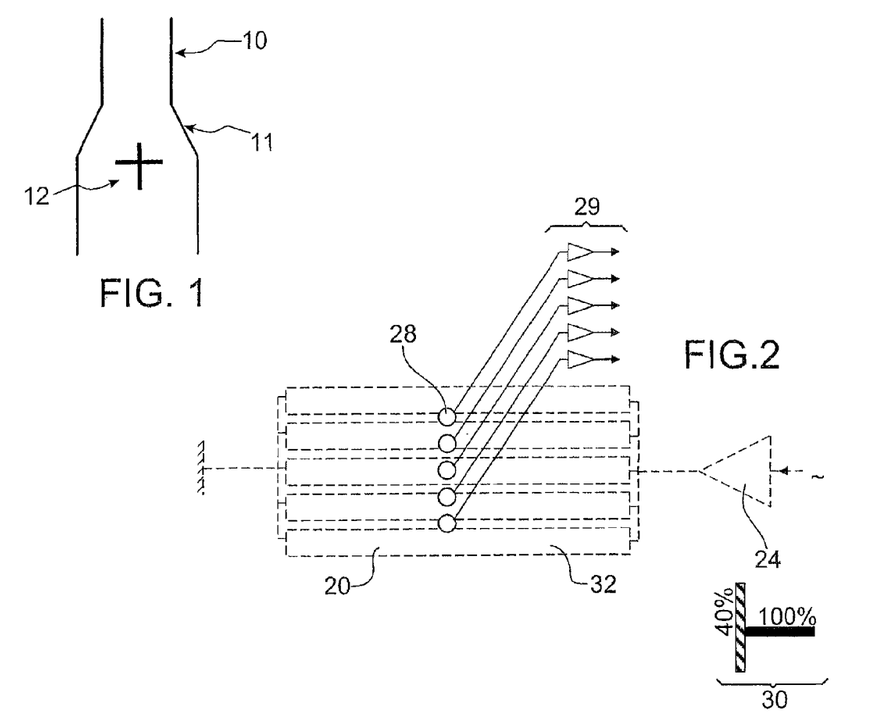
FIG. 1 diagrammatically illustrates the problem of inspection in a steam generator tube.
FIGS. 2 and 3 show two embodiments of the device according to the invention.

FIG. 1 diagrammatically illustrates such an inspection problem in a steam generator tube 10 with an expansion transition zone 11 and a complex defect 12.

Commercial sensors already exist to inspect steam generator tubes on site. They may be of a single element or multi-element type. However, these sensors are not very efficient for the detection of a transverse component of a complex defect, since the response of the longitudinal component is frequently preponderant and then conceals the complete signature of the complex defect. But it is important to be able to detect all transverse defects because this type of defect can cause a tube rupture (guillotine effect). Furthermore, a parasite signal can occur when passing over an expansion transition zone, even though the sensor could be fitted with a spring system that forces it into contact with the internal surface of the tube.

Document reference [1] at the end of the description discloses an apparatus and a process for a non-destructive measurement of a material to be tested using sensors that apply electromagnetic fields to this material and detect variations in the electromagnetic fields due to the proximity and properties of this material.

The purpose of this invention is the detection of at least one defect in a concave or convex structure capable of overcoming these disadvantages firstly by using an oriented current layer in emission to induce currents parallel to longitudinal defects in a tube, and secondly using flexible supports in reception, on which receivers are etched or added.

PRESENTATION OF THE INVENTION

The invention relates to a device for the detection of at least one defect in a concave or convex structure comprising an emitting part and a receiving part, characterised in that the emitting part comprises two current layers of several conducting strands, arranged at $+\theta°$ and $-\theta°$ relative to the horizontal plane and in that the receiving part comprises at least one magnetic field receiver added on or etched on a flexible receiving support.

The receivers may be coils, magnetic receivers (GMR, AMR, GMI, Fluxgate, TMR, Hall effect, etc.) or a combination of different types of such receivers. The orientation of the receivers may be variable.

Figure 11:
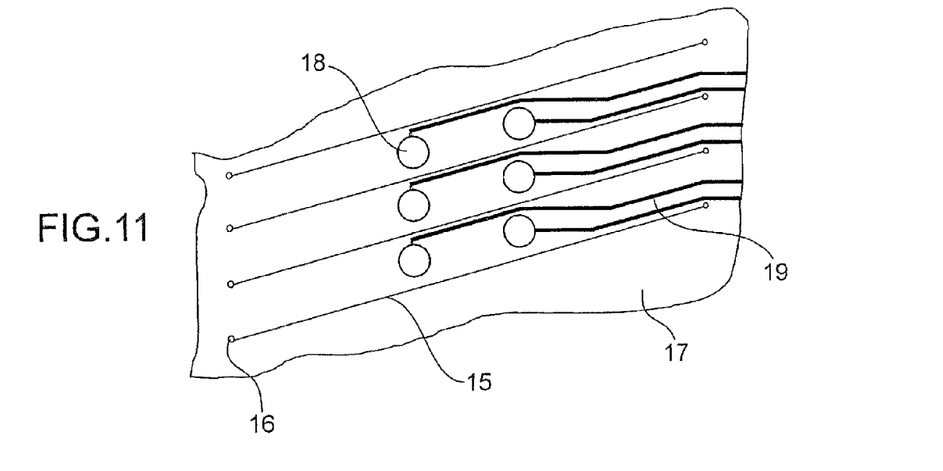
FIG. 11 shows the receiving part with slits.

Advantageously, as shown in FIG. 11, the flexible film of the receiving part comprises slits 15 that conform with variations in the tube diameter (R2), advantageously with holes 16 arranged at the ends of the slits 15 to prevent the flexible support from splitting, and it is placed on a foam or a spring device that forces the flexible support 17 into contact with the internal surface of the structure to be inspected, with coils 18 and connections 19.

In one embodiment, the device according to the invention comprises a current layer oriented along the axis of the defects whose influence is to be minimised (through longitudinal defects in the case of a steam generator tube) and to maximise the effect of other defects (transverse defects in the case of a steam generator).

In one embodiment, the emitting part comprises two current layers arranged at + or $-\theta$ relative to the axis of the defects whose influence is to be minimised. Thus, currents induced in the structure may be oriented at an angle of + or $-\theta$, for example 10°, by varying the amplitude of the power supply voltages of the two layers, so that the same probe can be used if the defects whose influence is to be minimised are not oriented precisely on the same axis.

Each layer of the emitting part may be placed on a rigid body or on a flexible support.

Advantageously, each current layer of the emitting part comprises a set of identical conducting strands parallel to each other connected in series or in parallel, an amplifier supplying sinusoidal current to each layer. A resistance may be associated in series with each conducting strand.

Advantageously, the receivers of the receiving part are associated with low noise amplifiers.

A part made of a rigid or flexible magnetic material (such as magnetic tape) may be placed between the emitting part and the return wires.

Advantageously, the receiving part comprises receivers placed in at least two columns staggered relative to each other.

The technology of coils etched on the flexible support, for example made of kapton, makes it possible to optimise matching to the surface of the structure to be inspected while guaranteeing good detection of defects due to minimisation of the air gap. The flexible probe thus made can improve defect detection and characterisation of this type of configuration, under difficult conditions such as a variation in the radius of curvature of the surface to be inspected.

DETAILED PRESENTATION OF PARTICULAR EMBODIMENTS

The first embodiment of the device according to the invention shown in FIG. 2 can induce eddy currents in a tube. It comprises an emitting part including at least one current layer 20 composed of a set of identical and parallel conducting strands 32 connected in series or in parallel creating a magnetic field under the layer 20 emitted almost uniformly in amplitude and in orientation. An amplifier 24 supplies sinusoidal current to the layer 20. The receiving part comprises coils 28, for example etched on a kapton film. Each of these coils may be associated with a low noise amplifier 29. The current layer 20, when it is oriented along the axis of a tube, can induce currents parallel to longitudinal defects in this tube.

Figure 3:
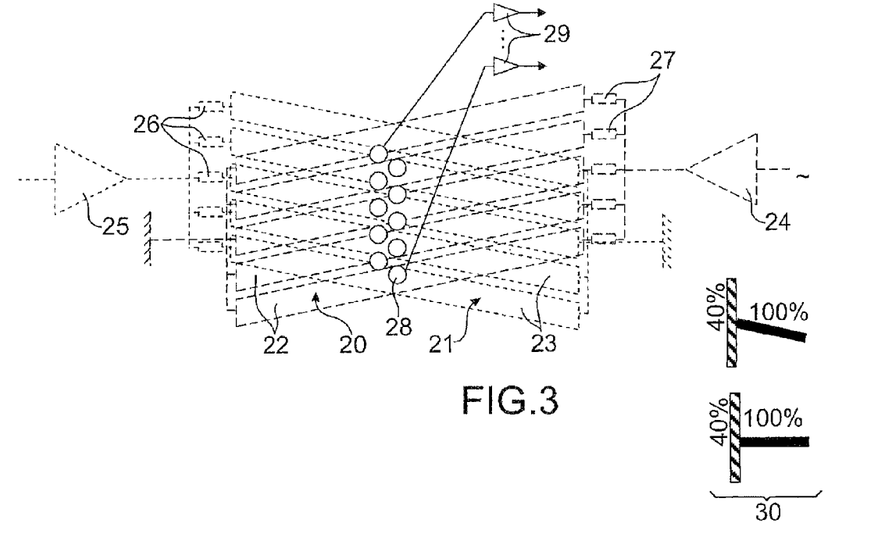

In a second embodiment shown in FIG. 3, the device according to the invention comprises an emitting part including two current layers 20 and 21 of several strands 22, 23 each layer being used with an amplifier 24 and 25. These current layers 20 and 21 are arranged at + and −10° relative to the horizontal plane, so that the orientation of the resultant layer can be adjusted by varying the amplitudes of power supply signals with the same frequencies. In this embodiment, the two layers are each etched on a flexible support made of kapton. Since their diameter inside the probe is fixed, it is possible to wind them on a rigid core. But the resistances of the strands during manufacturing of the printed circuit may be different, which makes the emitted field non-uniform. Insertion of a resistance 26, 27 in each strand 22 or 23 contributes to making the current in the different strands uniform, the current then being essentially fixed by the resistance. The receiving part comprises coils 28 staggered on two columns so as to increase the spatial resolution of the device according to the invention. Each receiver 28 has a low noise amplifier 29. The reference 30 shows complex defects.

Figure 4A:
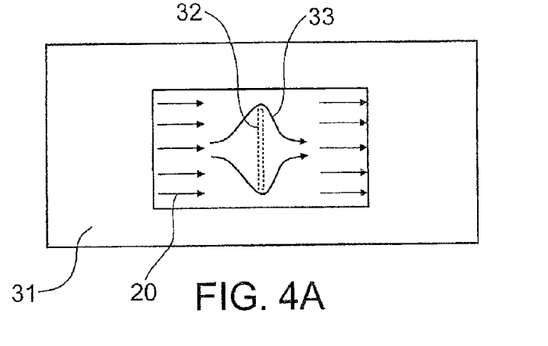
FIGS. 4A and 4B are top and side views respectively showing the deviation in induced currents for an external transverse defect.
Figure 4B:
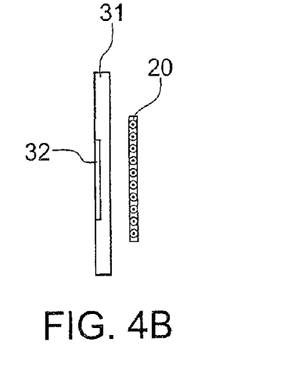
Figure 5A:
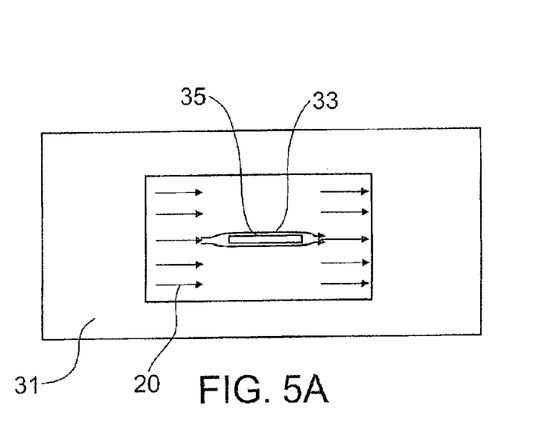
FIGS. 5A and 5B are top and side views respectively showing the deviation in induced currents for a through longitudinal defect.
Figure 5B:
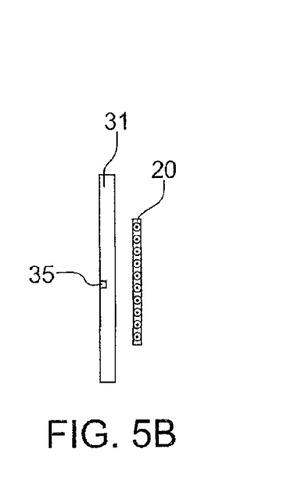
Figure 6A:
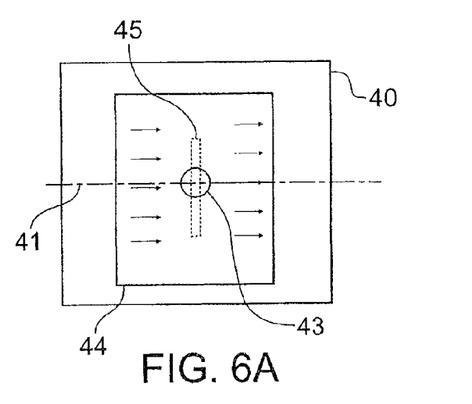
FIGS. 6A and 6B, and 7A and 7B show diagrams for basic configurations as a function of the frequency, for a 40% external defect and a 100% external defect respectively.
Figure 6B:
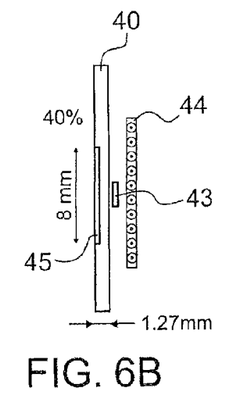
Figure 7A:
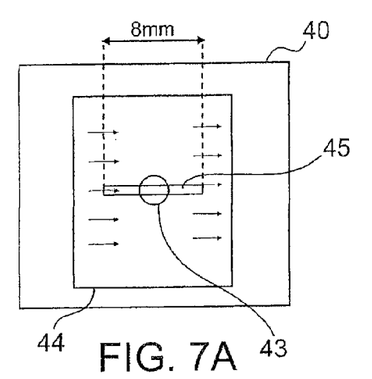
Figure 7B:
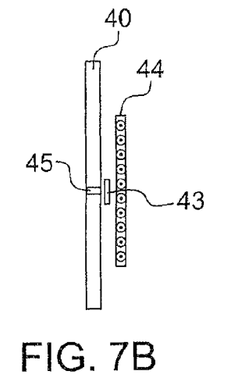

We will start by describing the first embodiment of the device according to the invention. FIGS. 4A and 4B diagrammatically show the path of induced currents in the presence of two components of a 40% external transverse defect taken separately, in a top view and side view respectively. These figures show a tube 31, the layer 20, a defect 32 and the induced currents 33. FIGS. 5A and 5B show similar views for a through longitudinal defect 35. Compared with the response due to the 40% external transverse defect, the fact that the longitudinal defect is a through defect which intuitively would be expected to give a strong radiated magnetic field, is compensated by the fact that the deviation of induced currents for this defect is very low.

Experimental results show the advantage of the first embodiment of the device according to the invention for detection of a transverse defect in the presence of a longitudinal defect. The receiving part comprises micro-coils. The layer of the emitting part and the micro-coils in the receiving part are etched on kapton films in order to benefit from the flexibility of this flexible support.

Optimisation of the Parameters in the Device According to the Invention

FIGS. 6A and 6B, 7A and 7B show a basic configuration used for all simulations for a transverse defect with a height of 40% of the thickness of the tube (FIGS. 6A and 6B), and for a through longitudinal defect with axis parallel to the orientation of the layer (FIGS. 7A and 7B) respectively. These figures show a tube 40, the axis 41 of this tube, a receiving coil 43 and a current layer 44, and a defect 45.

Figure 8A:
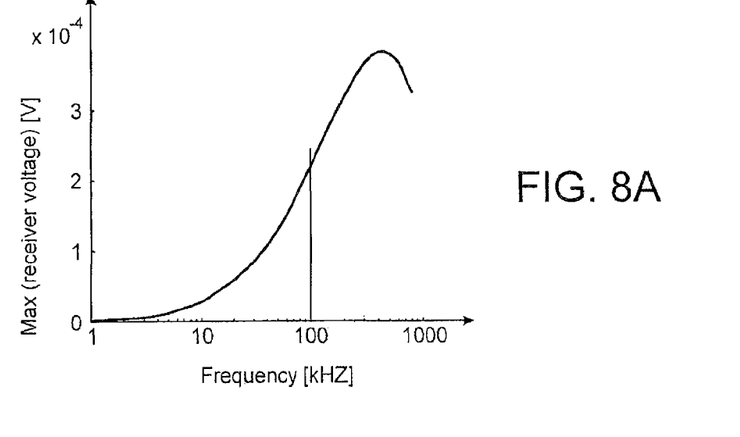
FIGS. 8A, 8B and 8C show curves showing basic configurations as a function of the frequency for a maximum amplitude of the response to a 40% transverse defect as a function of the frequency, maximum amplitude of the response to a through longitudinal defect, and the ratio of the two previous quantities for the transverse defect and the longitudinal defect as a function of the frequency, respectively.
Figure 8B:
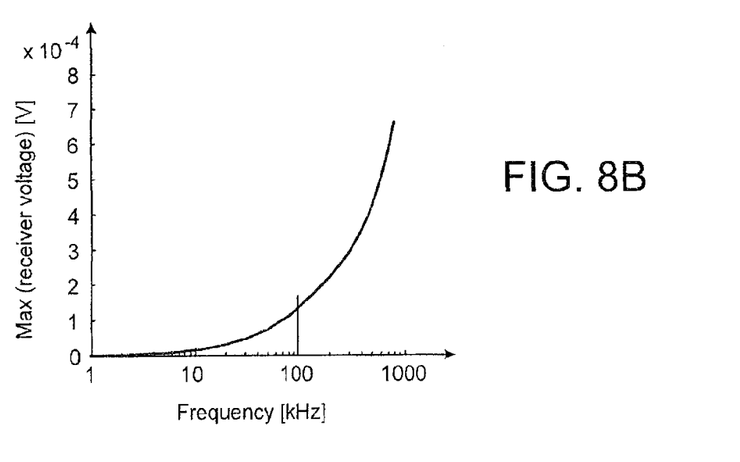
Figure 8C:
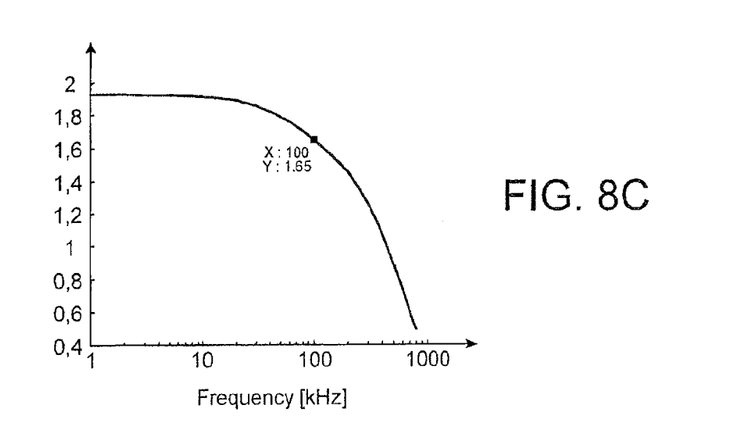

This embodiment uses a working frequency greater than or equal to 100 kHz. Frequencies of 240 kHz and 600 kHz can thus be used. The transverse contribution of the complex defect at these frequencies is better than in the case of the use of a conventional probe in separate functions mode and is much better when the frequency is low (see FIGS. 8A, 8B and 8C).

1. Emitting Part

Figure 9A:
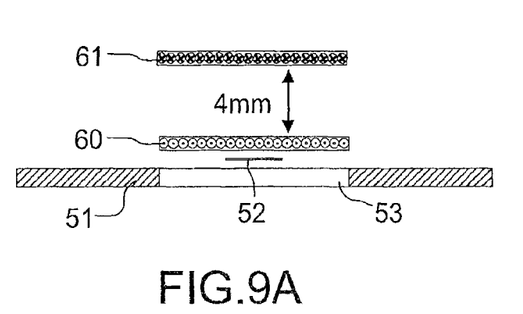
FIGS. 9A and 9B show a configuration of the device according to the invention in position on the structure to be inspected.
Figure 9B:
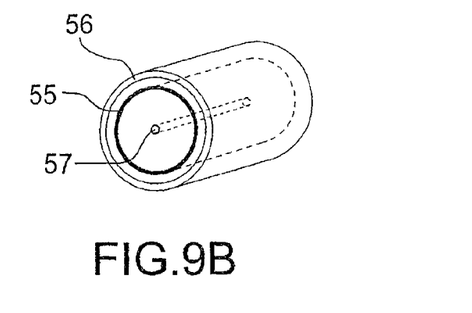

FIGS. 9A and 9B show a configuration of the device in position on the structure to be inspected: the emitting part is composed of a layer 55 with a fixed diameter on the internal periphery of the tube 56 (note the absence of any edge effect of the layer in this arrangement), the power supply return wires 57 passing through the centre of the tube. (The receiving part is referenced 52).

Figure 10A:
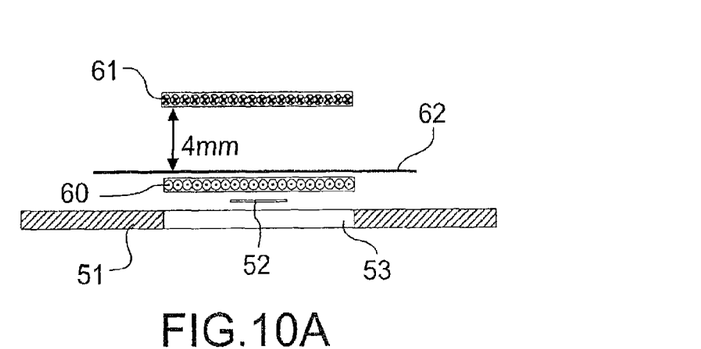
FIGS. 10A, 10B and 10C illustrate a configuration of the device according to the invention in position on the structure to be inspected, after inserting a magnetic tape (FIGS. 10A, 10B) and an experimental curve corresponding to the detection of a 10 mm long defect with and without magnetic tape.
Figure 10B:
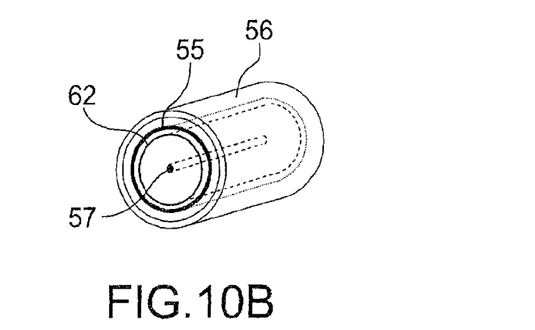
Figure 10C:
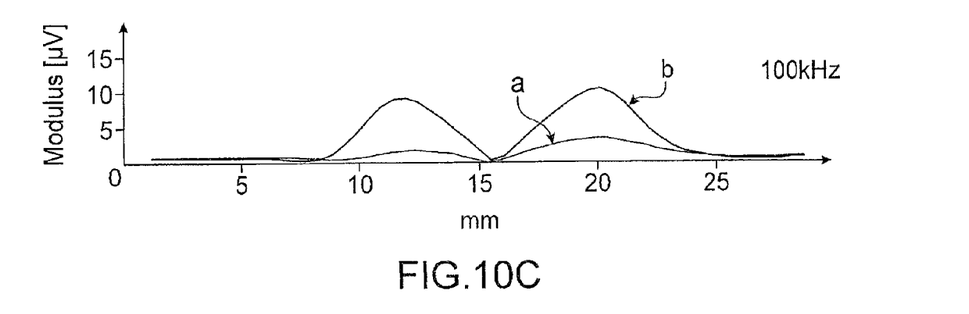

Since the current in the layer 55 is necessarily the same as in the power supply return wires 57, these wires 57 might generate a magnetic field that opposes the field created by the layer 55 itself. If a rigid or flexible magnetic material part 62 (for example made of a nanocrystalline material) is inserted between the emitting part (layers 60 and 61) and the return wires 57, and if for example it is placed as close as possible to the emitting part as shown in FIGS. 10A and 10B, the tape 62 cancels out the effects of the power supply return and amplifies the magnetic field emitted by the layer 55. FIG. 10C contains two experimental curves corresponding to detection of a 10 mm long defect, firstly in the absence of the magnetic part between the layer and the return of the conductors in the layer (curve a), and secondly in the presence of a magnetic tape made of a nanocrystalline material arranged above the layer (curve b). It can be seen that the signature of the defect is amplified by the presence of the magnetic part, due to the increase in the magnetic field radiated by the layer. Therefore this tape 62 is very beneficial.

Figure 12A:
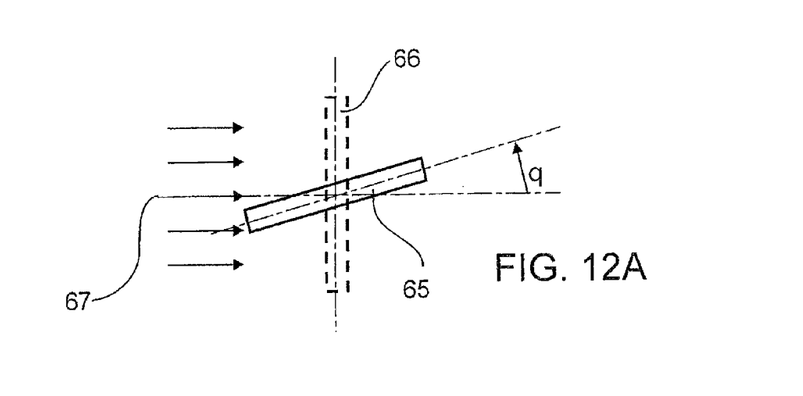
FIGS. 12A and 12B show a variation in the disorientation of a longitudinal defect at 100 kHz.
Figure 12B:
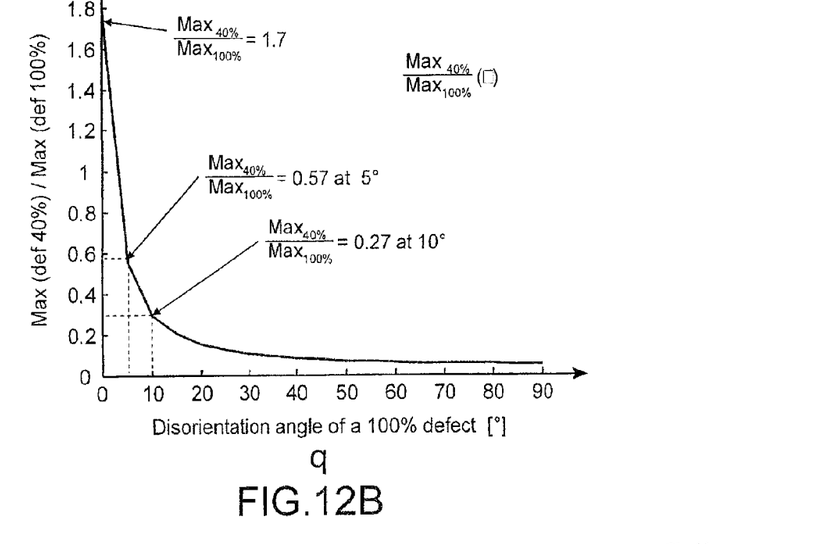

The emitting part comprises a current layer type induction coil that minimises the response of longitudinal defects when the direction of the layer is parallel to the direction of the defect (see FIGS. 12A and 12B). A disorientation of the longitudinal defect by a few degrees causes an important increase in the amplitude of the signature due to the longitudinal contribution of the complex defect. The response to the longitudinal defect then becomes greater than the response due to the transverse defect, which is a big problem for the device according to the invention. Therefore, it is useful to be able to adjust the orientation of the layer.

Figure 13:
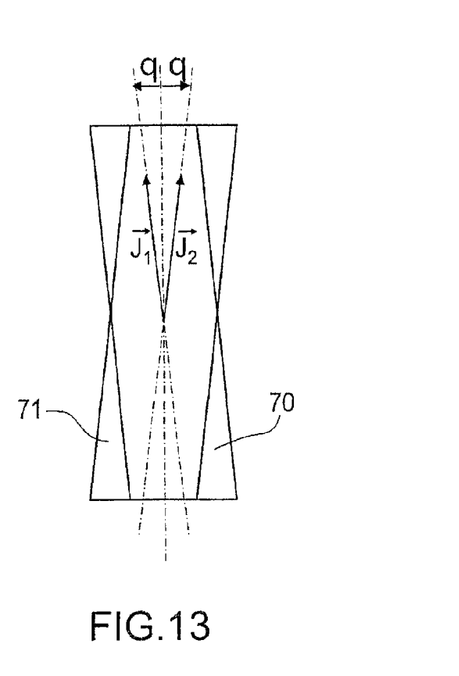
FIG. 13 shows the arrangement of two layers, with a disorientation of + and −θ.

Therefore we will consider two emitting layers 70, 71 arranged one above the other and disoriented by +10° and −10° from the axis of the tube 72 as shown in FIG. 13 (in the case in which it is assumed that in practice, a so-called longitudinal notch for which the effect is to be minimised can be created with an extreme orientation of between −10° and +10° relative to the tube axis), which corresponds to the second embodiment illustrated in FIG. 3. The eddy currents in the tube can then be oriented as required, by varying the power supply voltages in each of the layers 70 and 71 in order to reduce the influence of the longitudinal defect on detection of the transverse defect. A configuration with two layers oriented at 90° from each other is also possible and can orient the currents in all directions (R4). In order to obtain a satisfactorily uniform current, each of the two layers 70 and 71 identified in FIG. 13 is for example composed of 16 elementary strands identified in FIG. 14, in series with a resistance 73 of a few ohms selected to obtain an approximately identical current in each of the strands. Some strands are associated in parallel and others are in series, as shown in the diagram in FIG. 14, in order to give an impedance well matched to the power supply source, with a loop 74 through the axis of the tube. The power supply current 75 of the order of 100 mA, is output by two buffers located in the body of the device according to the invention.

Figure 25:
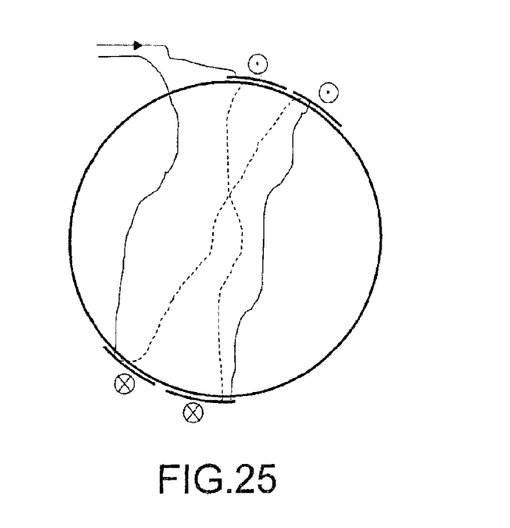
FIG. 25 illustrates a configuration of forward and return strands in a layer on the periphery of a cylinder.

The layer may also be in other configurations with forward strands on a peripheral portion of the cylinder and the same number of return strands arranged elsewhere on the periphery, for example on the diametrically opposite portion as shown in FIG. 25 for two forward strands and two return strands, all arranged in series. In this case, only the zones under the layers can be used. Since the receivers can then not cover the entire periphery, this configuration can be used when making a rotating probe containing a few receivers.

2. The Receiving Part

Figures 14, 15A:
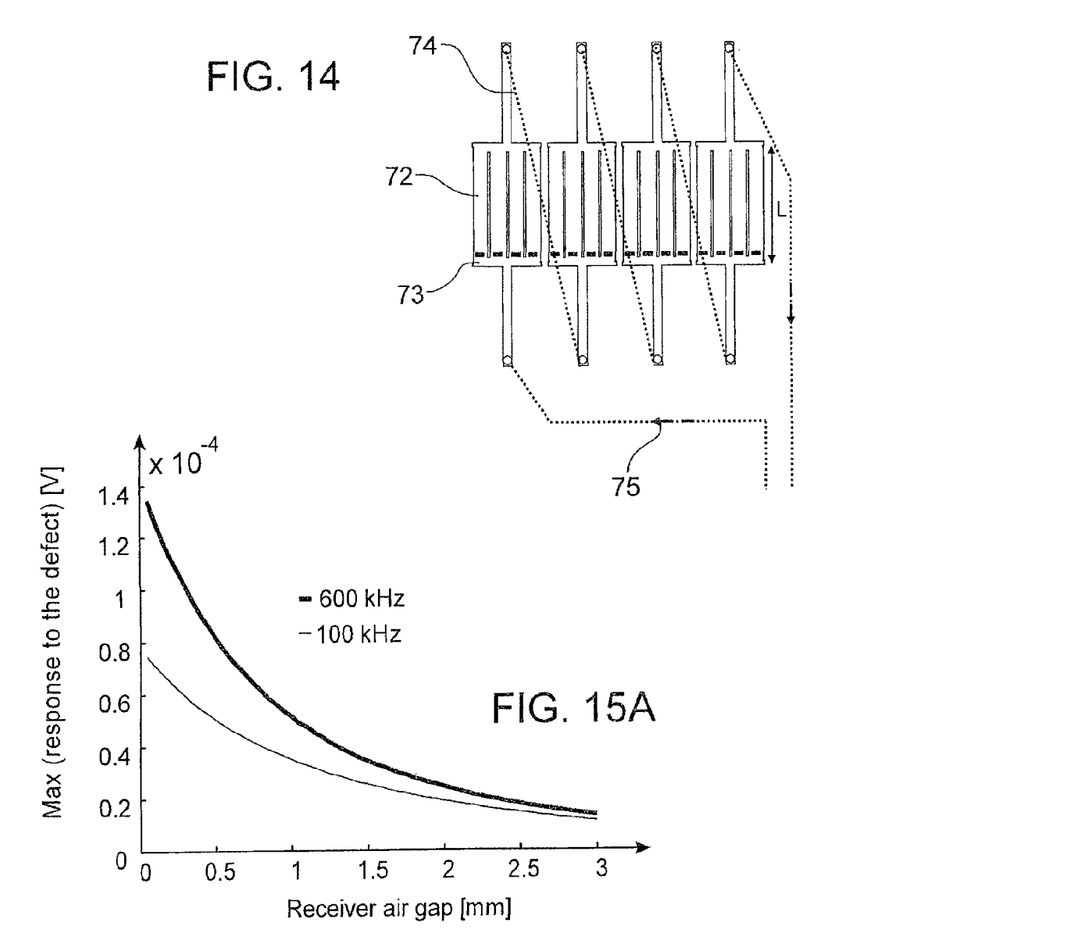
FIG. 14 is a diagram showing how some strands of a current layer or a set of strands are put into series and/or in parallel.
FIGS. 15A and 15B show the influence of the air gap of a receiver.
Figure 15B:
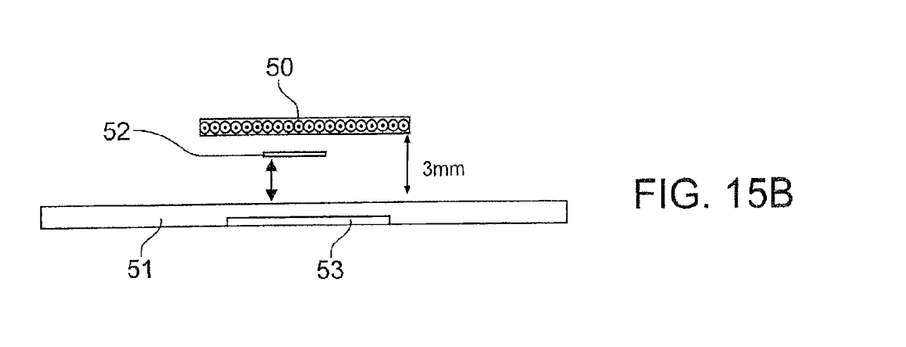

The influence of the air gap between the receiver and the part (tube) on the response to defects is shown in FIGS. 15A and 15B, the air gap of the layer then being fixed at 3 mm. The response of the receivers is very sensitive to this air gap, unlike the emitters that are not very sensitive to the air gap between the emitting part and the part being tested. The receiver 52 must be as close to the surface of the tube as possible and in particular the air gap must be constant while the device according to the invention is being displaced so that the air gap variation signal does not disturb the signal due to defects.

The device according to the invention may include a limited or a large number of receivers, and the probe is displaced over the surface of the part, to inspect the entire surface of the structure with a limited number of passes. When inspecting a tube, either a sufficient number of receivers are distributed around the entire circumference of the probe and the probe is displaced along the axis of the tube, or a few receivers are used (advantageously of different types and with different orientations) and the probe is moved spirally so as to inspect the entire internal surface of the tube. In all cases, the result is a map with a good spatial resolution so that post-treatments can be performed.

Figure 16A:
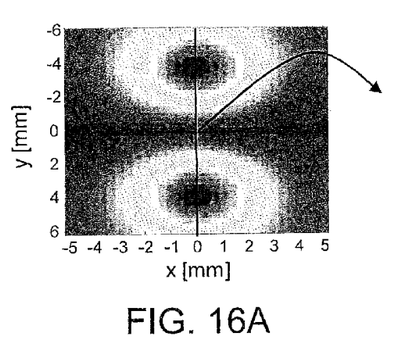
FIGS. 16A and 16B, and 16C and 16D show the determination of the minimum spacing between receivers, for a response to a 40% transverse defect and for a 100% longitudinal defect, respectively.
Figure 16B:
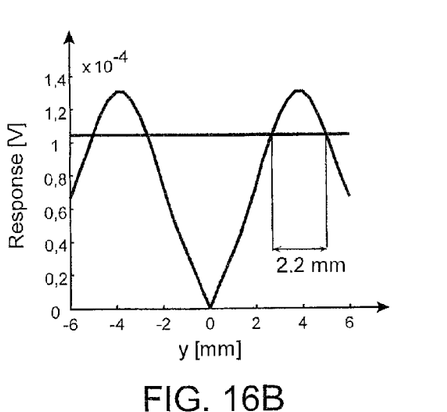
Figure 16C:
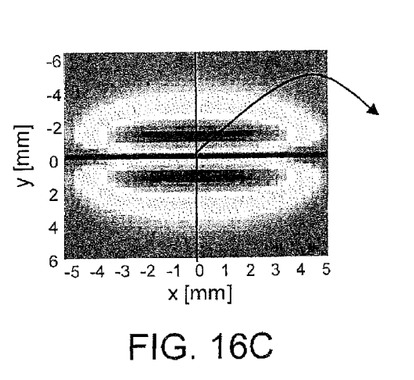
Figure 16D:
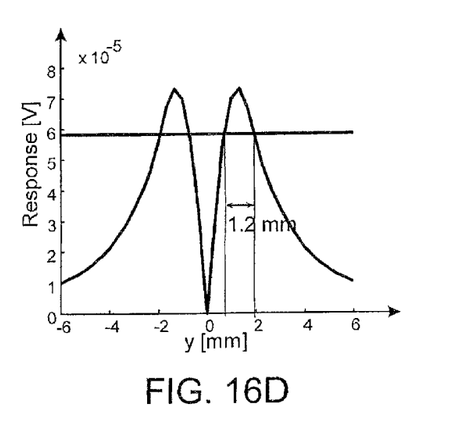

The simulations shown in FIGS. 16A and 16B and secondly in FIGS. 16C and 16D show the extraction of a line from the map of a 40% external transverse defect and extraction of a line from the map of a 100% longitudinal defect along the Y axis, passing through the maximum of each map, these simulations being done at 100 kHz.

The pitch between two adjacent receivers is less than 1.2 mm (taken at 80% of maximum amplitude) to detect complex defects in the tube, and therefore to obtain a sufficient spatial resolution even for the signature of the 100% longitudinal defect. A measurement pitch of about 1 mm is fixed for a tube quarter probe by providing 64 receivers (2 lines of 32 receivers) distributed around the entire periphery of the tube.

Figure 17A:
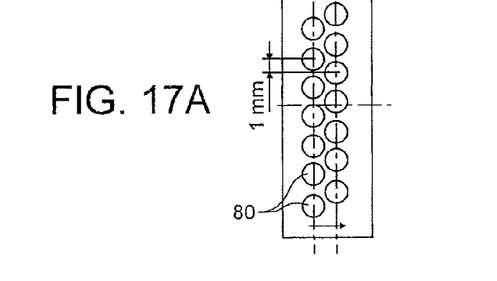
FIGS. 17A, 17B and 17C show a map obtained taking account of the pitch between receivers, with 16 receivers shown in FIG. 17A, for a 40% transverse defect (FIG. 17B) and for a 100% longitudinal defect (FIG. 17C).
Figure 17B:
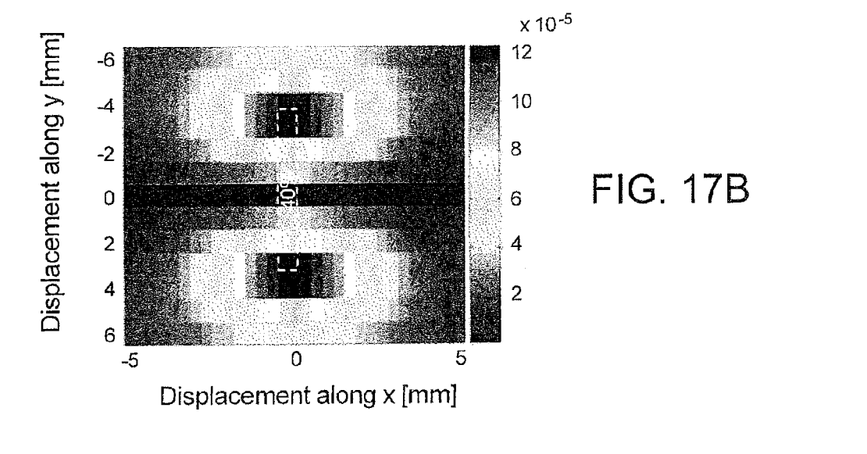
Figure 17C:
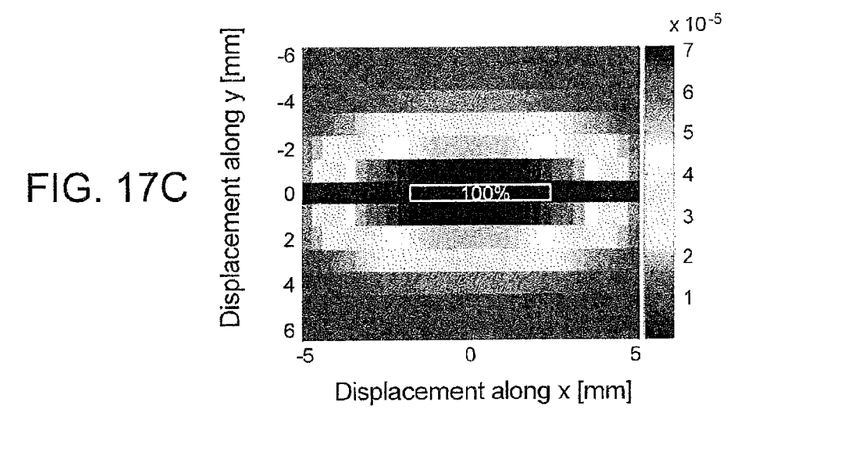

For dimensional reasons, the receiver coils 80 are arranged staggered on two lines, as shown in FIG. 17A. A mapping image simulated with this type of spacing between the receivers, with a 40% through defect and a 100% longitudinal defect respectively, is given in FIGS. 17B and 17C in the case of a prototype quarter tube probe with 16 receivers.

Receivers other than coils can also be used, since coils can only measure the component of the magnetic field normal to the tube. For example, magnetic receivers (GMR, GMI, AMR, FluxGates, Hall effect, etc.) can be used. These components may be etched or added onto a flexible film. They may also be chosen or oriented so as to measure the magnetic field due to the defect along the tube normal, axial or hoop component. An association of several receivers is possible inside a single probe (in a rotating or multi-element version) to detect different defects. In particular, the use of GMR for which the sensitive axis is oriented along the hoop direction can optimally detect 360° hoop defects, although such a defect would not be detected by measuring the normal component of the field.

3. Summary

Figure 18:
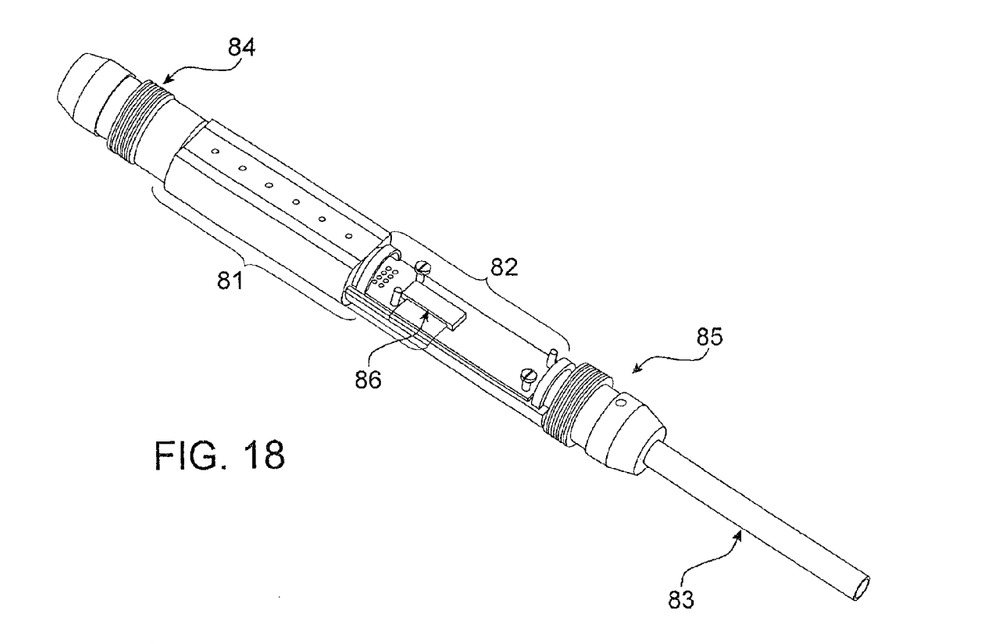
FIG. 18 shows a diagram of an embodiment of the device according to the invention.

The above elements give the main geometric characteristics of the device according to the invention and define the specifications of the different parts of the probe shown in FIG. 18, and particularly:

the different kapton+magnetic tape+foam 81: kapton with the receiving coils and kapton with the two layers at + and −10°, the electronics 82 onboard the device according to the invention; two layer power supply buffers and one preamplifier for each receiving coil, the connection cable 83 that is connected to the data processing apparatus, the body of the probe comprising two centring rings 84, 85, and a receiver—layer connector 86.

EXAMPLE EMBODIMENT

Figure 19:
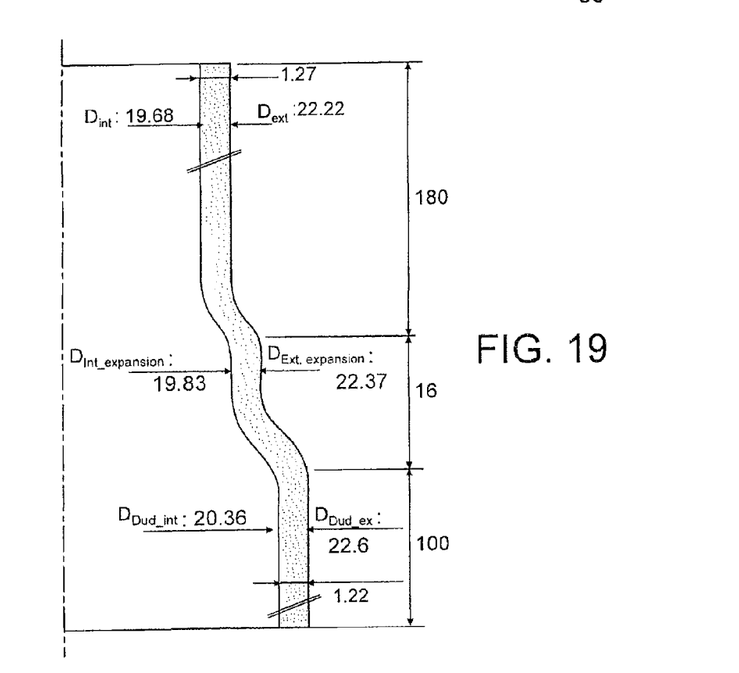
FIG. 19 shows the dimensional characteristics of an example embodiment of reference half-tubes.

An Inconel 600 half-tube with diameters identical to the diameters of the tubes of a 900 MW steam generator was made to test the device according to the invention. It comprises a deformation zone, in which the chosen geometric dimensions are severe (see the dimensional characteristics shown in FIG. 19). The inside diameter of the half-tube in front of and behind the deformation zone varies from 19.68 mm to 20.36 mm.

Figure 20A:
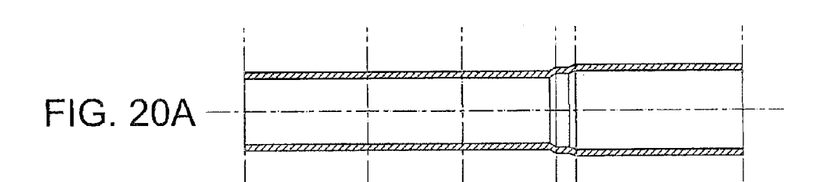
FIGS. 20A, 20B, 20C and 20D illustrate diagrams of reference half-tubes.
Figure 20B:
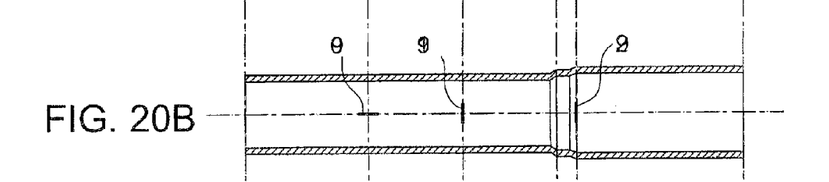
Figure 20C:
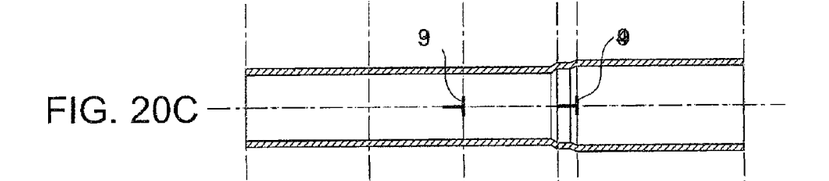
Figure 20D:
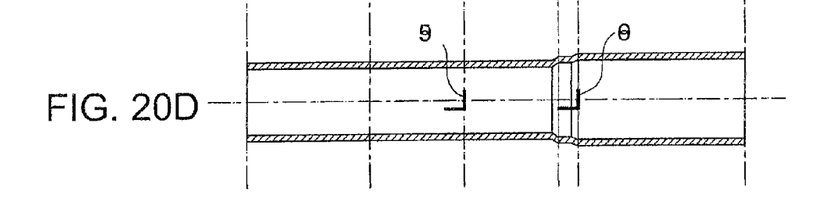

FIG. 20 contains a description of the half-tube. Simple defects were implanted on the half tube. These defects were made by electro-erosion, namely:

| Half tube | Specificities |
|---|---|
| FIG. 20B | Three simple defects 90, 91, 92: |
| | 100% longitudinal in a typical part |
| | 40% transverse in a typical part |
| | 40% transverse in an expansion transition zone |

In this example embodiment, the two layers at + and −10° and two series of resistances (one series per layer) are used on the emitting kapton film (induction coil). 16 coils (double-sided) and the connector are used on the receiving kapton film. Notches are formed in the kapton film so that it can adapt to variations in the tube diameter. The receiving kapton film is squeezed onto a piece of foam, which enables the receiving kapton film to match deformations.

The electronic part comprises low noise amplifiers for each receiver, and buffers to supply power to the two layers. The probe thus formed has centring rings at each of its ends so that it can be held in place in the tube.

The good mechanical behaviour of the receiving coils of the kapton film that opens in the form of a corolla when passing over a deformation zone is verified visually using a plexiglass tube with exactly the same diameter as the steam generator tube with a deformation zone.

The experimentally implemented conditions are as follows:

treatment apparatus used: M2M 64-channel MultiX eddy current apparatus, injection: 30 mA per strand for the inside layer and 25 mA per strand for the outside layer, frequency: 240 kHz, gain: 50 dB.

Figure 21:
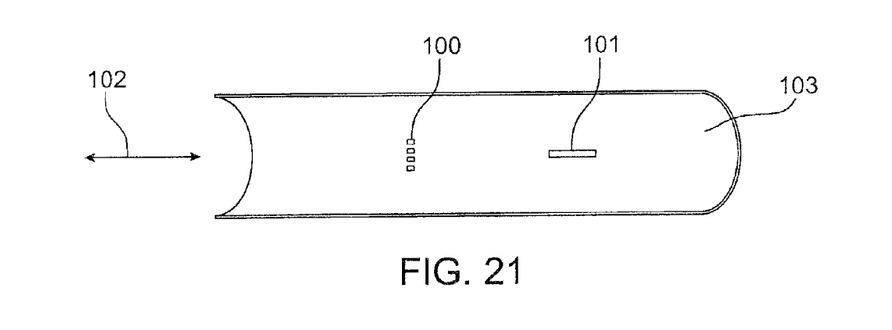
FIG. 21 illustrates a diagram of an inspection configuration on a reference half-tube.

The tests are done in the typical part of the half-tube (as shown in FIG. 21), on a 6 mm long 40% percent external transverse notch 100 and a 7 mm long 100% longitudinal notch with a displacement 102 of the probe, 103 representing the tube. This verifies that the probe made in this way gives correct signals corresponding to what is expected for detections of simple defects (longitudinal and transverse).

Figure 22A:
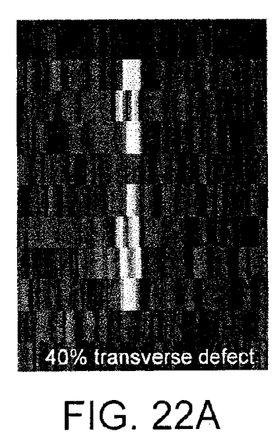
FIGS. 22A and 22B illustrate maps obtained with a longitudinal defect and with a transverse defect at 240 kHz respectively.
Figure 22B:
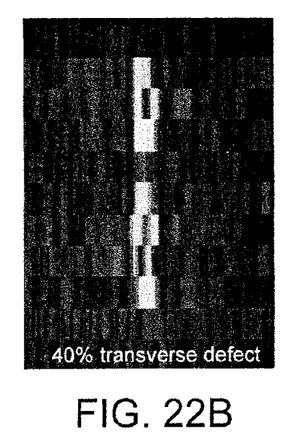
Figure 23:
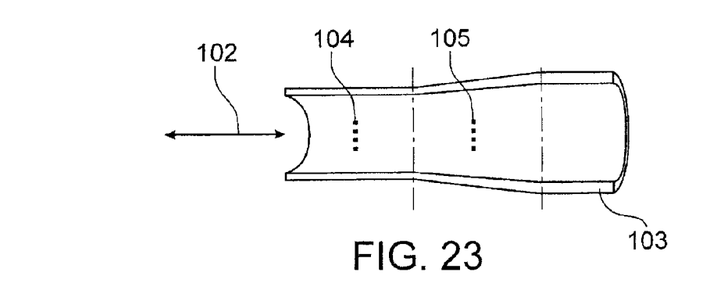
FIG. 23 illustrates a measurement configuration.

FIGS. 22A and 22B show the map obtained at 240 kHz for inspection with the probe in the half-tube No. 2. The first observation is the 40% transverse defect 104 in the plane part, followed by the same defect 105 in the deformation zone, as shown in FIG. 23. The signatures of the two defects are similar. It can be seen firstly that the maximum amplitudes are of the same order of magnitude, and secondly that no signal due to the deformation zone appears although the geometric characteristics of the deformation zone are severe.

Figure 24A:
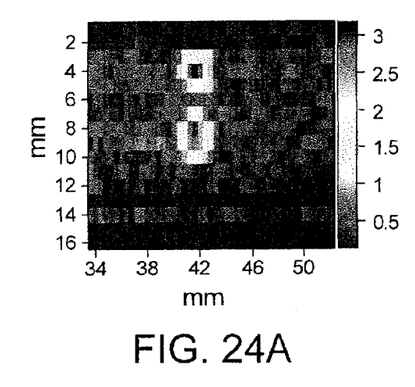
FIGS. 24A and 24B illustrate the comparison of experimental data (FIG. 24A) and simulated data (FIG. 24B) for a 40% transverse defect at 240 kHz.
Figure 24B:
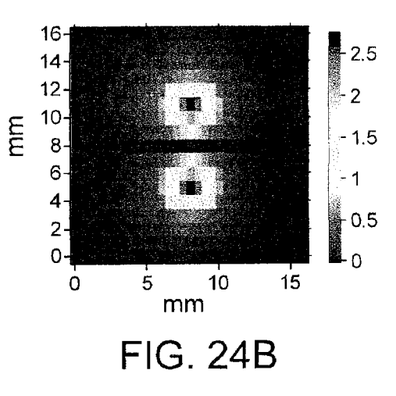

FIGS. 24A and 24B show a comparison of the modulus between the experimental data and simulated data for the isolated 40% external transverse defect. The abscissa axis is corrected, particularly by taking account of the offset between the two lines of receivers. It can be seen that the data agree well, and it is thus checked that the association of the foam and the kapton with notches is capable of perfectly following the deformation zones that are actually 3D (three dimensions) deformation surfaces. The results show that the device according to the invention reacts well to the defects that are to be detected.

REFERENCE

[1] U.S. Pat. No. 7,049,811

The invention claimed is:

1. A device for detection of at least one defect in a concave or convex structure comprising:
    an emitting part and a receiving part,
    wherein the emitting part comprises an oriented current layer to induce currents parallel to the axis of the at least one defect, said oriented current layer comprising two current layers of plural conducting strands, one of the two current layers being arranged at $+\theta°$ and the other current layer at $-\theta°$ relative to said axis, the orientation of the oriented layer being adjusted by varying amplitudes of power supply signals of these two layers, and
    wherein the receiving part comprises at least one magnetic field receiver added on or etched on a flexible receiving support.

2. A device according to claim 1, in the at least one magnetic field receiver is a coil.

3. A device according to claim 1, in which the at least one magnetic field receiver is a magnetic receiver with a sensitive axis oriented relative to the structure.

4. A device according to claim 1, in which each layer of the emitting part is arranged on a flexible support.

5. A device according to claim 1, in which each flexible receiving support comprises slits with a hole at each end of the slits, and is squeezed onto a piece of foam.

6. A device according to claim 1, in which $\theta=10°$.

7. A device according to claim 1, comprising two layers oriented at 90° from each other so that currents can be oriented in all directions.

8. A device according to claim 1, in which each current layer of the emitting part comprises a set of identical conducting strands, parallel to each other some being connected in series and others in parallel.

9. A device according to claim 8, comprising a resistance in series with each strand.

10. A device according to claim 1, in which an amplifier supplies sinusoidal current to each current layer in the emitting part.

11. A device according to claim 1, in which the at least one magnetic field receiver is associated with a low noise amplifier.

12. A device according to claim 1, comprising a part made of magnetic material placed between the emitting part and return wires.

13. A device according to claim 1, in which the receiving part comprises receivers placed on at least two columns staggered relative to each other.

14. A device for detection of at least one defect in a concave or convex structure comprising:

an emitting part and a receiving part, wherein the emitting part comprises two current layers of plural conductions strands, one of the layers being arranged at $+\theta°$ and the other at $-\theta°$ relative to an axis of the at least one defect, so that orientation of the resultant layer can be adjusted by varying amplitudes of power supply signals of the two current layers, and wherein the receiving part comprises at least one magnetic field receiver added on or etched on a flexible receiving film, which comprises slits with a hole at each end of the slits, and is squeezed onto a piece of foam.

* * * * *